United States Patent [19]

Pham et al.

[11] Patent Number: 6,099,694
[45] Date of Patent: Aug. 8, 2000

[54] AZEOTROPE-LIKE COMPOSITIONS OF DIFLUOROMETHANE AND CHLORINE

[75] Inventors: Hang Thanh Pham, Amherst; Rajiv R. Singh, Getzville; Addison M. Smith, Amherst; David P. Wilson, East Amherst; Raymond Hilton Percival Thomas, Pendleton, all of N.Y.; Gustavo Cerri, Parsippany, N.J.

[73] Assignee: AlliedSignal Inc., Morristown, N.J.

[21] Appl. No.: 09/046,095

[22] Filed: Mar. 23, 1998

Related U.S. Application Data

[63] Continuation-in-part of application No. 08/868,399, Jun. 3, 1997, abandoned
[60] Provisional application No. 60/020,181, Jun. 14, 1996.
[51] Int. Cl.[7] .............................. B01D 3/36; B01D 3/42; C07C 17/386; C07C 19/03
[52] U.S. Cl. .................... 203/3; 203/29; 203/67; 510/408; 570/166; 570/178
[58] Field of Search ............................... 203/3, 6, 22, 67, 203/29; 570/177, 178, 166; 510/408; 252/67

[56] References Cited

U.S. PATENT DOCUMENTS

| | | | |
|---|---|---|---|
| 3,694,362 | 9/1972 | Floria | 252/67 |
| 5,210,342 | 5/1993 | Moore | 570/179 |
| 5,495,057 | 2/1996 | Nam et al. | 570/167 |

FOREIGN PATENT DOCUMENTS

| | | |
|---|---|---|
| 0015637 | 5/1997 | WIPO. |

OTHER PUBLICATIONS

CA 121:136839: Vinogradov et al., Ah. Prikl. Kim., "Study of Azeotropic Properties in Systems formed by Khladon 21 and Khladon 22 with Chlorine and Hydrogen Fluoride", 1993, 66(10), 2389–92.

*Primary Examiner*—Virginia Manoharan
*Attorney, Agent, or Firm*—Jay P. Friedenson; Marie L. Collazo; Colleen D. Szuch

[57] ABSTRACT

The invention relates to an improvement in a process in which chlorine and difluoromethane are present in a distillation column, for example, a fluorination reaction. By controlling the chlorine feed such that the concentration of chlorine relative to difluoromethane in the distillation column is maintained below about 22 weight percent (the flammability threshold for chlorine in a mixture of difluoromethane and chlorine), formation of a flammable difluoromethane/chlorine mixture may be minimized or avoided. The invention is particularly useful in a process for the preparation of difluoromethane wherein at least one distillation column separates difluoromethane from unreacted starting materials such as methylene chloride, hydrogen fluoride and monochloromonofluoromethane.

5 Claims, No Drawings

AZEOTROPE-LIKE COMPOSITIONS OF DIFLUOROMETHANE AND CHLORINE

This application is a continuation-in-part of U.S. patent application Ser. No. 08/868,399 filed Jun. 3, 1997 (abandoned), which claims priority of Provisional Application Ser. No. 60/020,181 filed Jun. 14, 1996.

FIELD OF THE INVENTION

The present invention relates to mixtures of difluoromethane ("HFC-32") and chlorine. More particularly, the invention provides azeotrope-like compositions of HFC-32 and chlorine.

BACKGROUND OF THE INVENTION

Chlorine is used by industry in a number of processes including in the production of chlorinated organic and inorganic chemicals. For example, methane may be chlorinated to produce methylene chloride, chloroform, or carbon tetrachloride. As another example, hydrogen and chlorine may be reacted to produce hydrochloric acid.

However, these chlorination reactions are highly exothermic reactions which require close temperature control. Additionally, in the manufacture of chlorine itself, cooling of the reactant and product vessels are required. Therefore, a need exists for a reactant that will permit these reactants to be carried out under less exothermic conditions.

DESCRIPTION OF THE INVENTION AND PREFERRED EMBODIMENTS

This invention provides azeotrope-like compositions of HFC-32 and chlorine comprising an effective amount of HFC-32 and chlorine. By "effective amount" is meant an amount of each component that, when the components are combined, formation of an azeotrope or an azeotrope-like mixture results. Preferably, the azeotrope-like compositions of the invention comprise about 1 to about 60 weight percent chlorine and from about 99 to about 40 weight percent HFC-32 and have a boiling point of about 20°±about 4° C., preferably about 20°±1° C., at about 234 psia. The preferred, more preferred, and most preferred compositions of the invention are set forth in Table 1. The numerical ranges in Table 1 are to be understood to be prefaced by the term "about".

TABLE 1

| Components | Preferred (wt %) | More Preferred (wt %) | Most Preferred (wt %) |
|---|---|---|---|
| HFC-32 | 40–99 | 50–95 | 60–90 |
| Chlorine | 1–60 | 5–50 | 10–40 |

In a particularly preferred embodiment, the composition of the invention comprises an effective amount of HFC-32 and chlorine wherein the composition boils at about −55°±about 1° C. at about atmospheric pressure (745 mm Hg). In a still more particularly preferred embodiment, the composition of the invention comprises about 65±about 5 weight percent HFC-32 and about 35±about 5 weight percent chlorine which composition boils at about −55°±about 1.0° C.

For purposes of this invention, azeotrope-like compositions are compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant boiling and cannot be separated during a phase change.

Azeotrope-like compositions behave like azeotropic mixtures, i e., are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All compositions of the invention within the indicated ranges as well as certain compositions outside these ranges are azeotrope-like.

The azeotrope-like compositions of the invention may include additional components that do not form new azeotropic or azeotrope-like systems, or additional components that are not in the first distillation cut. The first distillation cut is the first cut taken after the distillation column displays steady state operation under total reflux conditions. One way to determine whether the addition of a component forms a new azeotropic or azeotrope-like system so as to be outside of this invention is to distill a sample of the composition with the component under conditions that would be expected to separate a nonazeotropic mixture into its separate components. If the mixture containing the additional component is nonazeotropic or nonazeotrope-like, the additional component will fractionate from the azeotropic or azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like, or constant boiling. All such compositions are intended to be covered by the terms "azeotrope-like" and "constant boiling". As an example, it is well known that at differing pressures, the composition of a given azeotrope will vary at least slightly as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

The compositions of the invention have a lower boiling point than either of the compositions' components. One ordinarily skilled in the art will recognize that the compositions of the invention may offer superior refrigeration capacity when compared to either chlorine or HFC-32 alone. Thus, in one embodiment of the invention, the azeotrope-like compositions of the invention may be used in a method for cooling. In a preferred embodiment, the compositions are used in method for cooling the reactant and product vessels in a process for producing chlorine.

In yet another embodiment of the invention, the compositions may find utility in chlorination reactions of organic and inorganic starting materials. The chlorination of these materials is highly exothermic and, by using the azeotrope-like compositions of the invention in place of chlorine in the chlorination reactions, the heat generated by the reactions may be lowered by a factor of from about 3 to about 6 depending on the HFC-32/chlorine ratio. Any organic or inorganic materials that may be chlorinated may be chlorinated using the compositions of the invention. Because the chlorination reactions of such materials are well known in the art, the reaction conditions and amounts of starting materials and of the azeotrope-like composition of the invention to be used will be readily ascertainable by one ordinarily skilled in the art.

In still another embodiment, the compositions of the invention may find utility in any reaction (such as a fluorination reaction) in which chlorine and HFC-32 are present in a distillation column in order to prevent the formation of flammable mixtures of chlorine and difluoromethane. It is known that combinations of HFC-32 and chlorine pose a potential flammability risk. The flammability threshold for chlorine in a mixture of HFC-32 and chlorine is about 22 weight percent. By controlling the chlorine feed such that the concentration of chlorine relative to difluoromethane in the distillation column is maintained below about 22 weight percent, all of the chlorine may be withdrawn from the top of the distillation column with HFC-32 in the form of the higher-boiling azeotrope-like compositions of the present invention. In this manner, the formation of the flammable HFC-32/chlorine mixture in the column may be minimized if not avoided. Thus the invention includes the following processes:

In a process for producing a fluorocarbon comprising the step of separating in a distillation column a product stream comprising difluoromethane and chlorine from a reaction mixture comprising a halide catalyst and chlorine, the improvement comprising adding chlorine to the reaction mixture at a rate such that the concentration of chlorine in the distillation column is maintained below the flammability threshold for a chlorine/difluoromethane mixture.

In a process comprising the step of separating in a distillation column a product stream comprising chlorine and difluoromethane from a reaction mixture comprising chlorine, the improvement comprising adding chlorine to the reaction mixture at a rate such that the concentration of chlorine relative to difluoromethane in the distillation column is maintained below the flammability threshold for a chlorine/difluoromethane mixture.

In a process for producing difluoromethane comprising the step of separating in a distillation column a product stream comprising difluoromethane and chlorine from a reaction mixture comprising methylene chloride (HCC-30), hydrogen fluoride and monochloromonofluoromethane (HCFC-31), a halide catalyst and chlorine, the improvement comprising adding chlorine to the reaction mixture at a rate such that the concentration of chlorine in the distillation column is maintained below the flammability threshold for a chlorine/difluoromethane mixture.

During the HFC-32 production process, at least one distillation column separates HFC-32 from unreacted starting materials, such as HCC-30 and hydrogen fluoride, and the reaction intermediate, monochloromonofluoromethane ("HCFC-31"). Because the boiling point of chlorine, −30° F., is between that of HFC-32, −61° F., and HCFC-31, −15.6° F., chlorine may build up to a high concentration in the middle of the distillation column even if chlorine is fed at a very low rate. It has been discovered that the HFC-32/chlorine azeotrope-like composition may be used for purging chlorine, along with HFC-32, from the distillation column. By controlling the chlorine feed, such that the concentration of chlorine in the distillation column is maintained below about 22 weight percent, all of the chlorine may be withdrawn from the top of the distillation column with HFC-32 in the form of the higher-boiling azeotrope-like compositions of the invention.

The components of the compositions of the invention are commercially available or may be produced by known methods. Preferably, the components are of sufficiently high purity so as to avoid the introduction of adverse influences on the properties, such as constant boiling, of the compositions.

The following non-limiting examples serve to illustrate the invention.

EXAMPLES

Example 1

An ebulliometer which consisted of a vacuum jacketed tube with a condenser on top was used. About 20.8 grams of difluoromethane was charged into the ebulliometer and chlorine was added in measured small increments. The temperature was measured using a platinum resistance thermometer. From about 0 to about 32 weight percent chlorine, the boiling point of the composition changed by only about 4° C. Therefore the composition behaves as a constant-boiling over this range.

Example 2

Table 2 shows the vapor pressure measurement of HFC-32 and chlorine as a function of composition of chlorine (weight percent chlorine) at constant temperature of about 20° C. From this Table it may be observed that at this temperature, the compositions at which the vapor pressure maximum is approximately 31.7 weight percent chlorine and between approximately 26.2 to 36.7 weight percent chlorine. The data also show that the vapor pressure of mixtures of HFC-32 and chlorine is higher, at all indicated blend proportions, than HFC-32 and chlorine alone, i.e. as indicated in the first and last rows when chlorine is 0.0 weight percent and HFC-32 is at 100.0 weight percent as well as when HFC-32 is at 0.0 weight percent and chlorine is at 100.0 weight percent.

TABLE 2

| WEIGHT PERCENT CHLORINE | PRESSURE (PSIA) |
| --- | --- |
| 0.0 | 213.4 |
| 6.5 | 221.5 |
| 9.8 | 224.7 |
| 15.8 | 229.3 |
| 20.6 | 231.8 |
| 26.2 | 234.3 |
| 31.7 | 234.3 |
| 36.7 | Z33.5 |
| 41.7 | 232.6 |
| 48.9 | 229.7 |
| 100.0 | 100.7 |

What is claimed is:

1. In a process comprising the stop of separating in a distillation column a stream comprising chlorine and difluoromethane from a mixture comprising chlorine, difluoromethane and unreacted starting materials the improvement comprises adding chlorine to the mixture at a rate such that the concentration of chlorine relative to difluoromethane in the distillation column is maintained below the flammability threshold for a chlorine and difluoromethane mixture of about 22 weight percent, and withdrawing difluoromethane and chlorine from the top of the distillation column.

2. The process of claim 1 wherein the mixture further comprises a catalyst.

3. The process of claim 2 wherein the catalyst is a halide catalyst.

4. The process of claim 1 wherein the unreacted starting materials comprise methylene chloride and hydrogen fluoride and the mixture further comprises monochloromonofluoromethane and a catalyst.

5. The process of claim 4 wherein the catalyst is a halide catalyst.

\* \* \* \* \*